(12) United States Patent
Kline et al.

(10) Patent No.: US 10,716,594 B2
(45) Date of Patent: Jul. 21, 2020

(54) DEVICES, SYSTEMS, AND METHODS FOR TISSUE SPECIMEN REMOVAL

(71) Applicant: COVIDIEN LP, Mansfield, MA (US)

(72) Inventors: Ashley N. Kline, Fishers, IN (US); Katherine M. Polednik, Broomfield, CO (US); Kevin D. Garman, Milwaukee, WI (US); Katherine S. Maxwell, Haslett, MI (US)

(73) Assignee: Covidien LP, Mansfield, MA (US)

( * ) Notice: Subject to any disclaimer, the term of this patent is extended or adjusted under 35 U.S.C. 154(b) by 414 days.

(21) Appl. No.: 15/620,068

(22) Filed: Jun. 12, 2017

(65) Prior Publication Data

US 2018/0353198 A1 Dec. 13, 2018

(51) Int. Cl.

| A61B 17/34 | (2006.01) |
|---|---|
| A61B 17/32 | (2006.01) |
| A61B 1/018 | (2006.01) |
| A61B 1/015 | (2006.01) |
| A61B 1/00 | (2006.01) |
| A61B 17/00 | (2006.01) |
| A61B 1/307 | (2006.01) |

(52) U.S. Cl.
CPC ...... *A61B 17/3421* (2013.01); *A61B 17/3439* (2013.01); *A61B 1/00154* (2013.01); *A61B 1/015* (2013.01); *A61B 1/018* (2013.01); *A61B 1/307* (2013.01); *A61B 17/32002* (2013.01); *A61B 2017/00287* (2013.01); *A61B 2017/320024* (2013.01); *A61B 2017/3441* (2013.01); *A61B 2017/3445* (2013.01)

(58) Field of Classification Search
CPC .. A61B 17/32002; A61B 2017/320024; A61B 17/3421; A61B 17/3439; A61B 1/018; A61B 1/307; A61B 17/22031; A61B 17/221; A61B 17/320725; A61B 2017/22034; A61B 2017/22035
See application file for complete search history.

(56) References Cited

U.S. PATENT DOCUMENTS

| 5,354,303 | A | * | 10/1994 | Spaeth | A61B 17/00234 604/171 |
|---|---|---|---|---|---|
| 5,370,647 | A | * | 12/1994 | Graber | A61B 17/00234 606/127 |
| 5,836,953 | A | | 11/1998 | Yoon | |

(Continued)

*Primary Examiner* — Aaron B Fairchild
(74) *Attorney, Agent, or Firm* — Carter, DeLuca & Farrell LLP

(57) ABSTRACT

A device facilitating removal of tissue includes a sheath and a deployable assembly deployable from the sheath. The deployable assembly includes a funnel, a proximal apex portion, a distal base portion, and a plurality of guards. Each guard defines a fixed end attached to a portion of an annular perimeter of the distal base portion of the funnel by a living hinge. In the deployed condition of the deployable assembly, the guards are disposed in a presented condition wherein the guards extend radially inwardly from the annular perimeter of the distal base portion of the funnel in overlapping relation relative to one another such that the guards extend across the distal base portion of the funnel to enclose an interior of the funnel. A containment bag for sealingly encapsulating the funnel therein is also provided as part of a system with the device. Methods of use are provided as well.

16 Claims, 5 Drawing Sheets

(56) References Cited

U.S. PATENT DOCUMENTS

| | | | |
|---|---|---|---|
| 6,156,055 A * | 12/2000 | Ravenscroft | A61B 17/221 |
| | | | 606/206 |
| 6,159,230 A | 12/2000 | Samuels | |
| 6,280,450 B1 * | 8/2001 | McGuckin, Jr. | A61B 17/221 |
| | | | 606/114 |
| 6,383,195 B1 | 5/2002 | Richard | |
| 2007/0118175 A1 * | 5/2007 | Butler | A61B 17/3423 |
| | | | 606/213 |
| 2007/0135820 A1 | 6/2007 | Que et al. | |
| 2007/0198045 A1 * | 8/2007 | Morton | A61B 17/3439 |
| | | | 606/191 |
| 2008/0312496 A1 | 12/2008 | Zwolinski | |
| 2009/0299363 A1 * | 12/2009 | Saadat | A61B 1/00135 |
| | | | 606/41 |
| 2010/0256523 A1 | 10/2010 | Uznanski et al. | |
| 2011/0264091 A1 | 10/2011 | Koppleman et al. | |
| 2012/0238816 A1 * | 9/2012 | Gunday | A61B 1/00135 |
| | | | 600/114 |
| 2013/0225934 A1 * | 8/2013 | Raybin | A61B 17/32056 |
| | | | 600/214 |
| 2014/0221949 A1 | 8/2014 | Aklog et al. | |
| 2014/0228875 A1 | 8/2014 | Saadat | |
| 2015/0297254 A1 | 10/2015 | Sullivan et al. | |
| 2015/0305772 A1 | 10/2015 | McCauley | |
| 2016/0030073 A1 | 2/2016 | Isakov et al. | |
| 2016/0045214 A1 | 2/2016 | Sullivan et al. | |
| 2016/0287275 A1 | 10/2016 | Honda | |

* cited by examiner

DEVICES, SYSTEMS, AND METHODS FOR TISSUE SPECIMEN REMOVAL

BACKGROUND

Technical Field

The present disclosure relates to tissue specimen removal and, more particularly, to devices, systems, and methods facilitating removal of a tissue specimen from an internal body cavity.

Background of Related Art

In minimally-invasive surgical procedures, operations are carried out within an internal body cavity through small entrance openings in the body. The entrance openings may be natural passageways of the body or may be surgically created, for example, by making a small incision into which a cannula is inserted.

Minimally-invasive surgical procedures may be used for partial or total removal of tissue from an internal body cavity. However, the restricted access provided by minimally-invasive openings (natural passageways and/or surgically created openings) presents challenges with respect to maneuverability and visualization. The restricted access also presents challenges when large tissue specimens are required to be removed. As such, tissue specimens that are deemed too large for intact removal may be broken down into a plurality of smaller pieces to enable removal from the internal body cavity.

During such minimally-invasive surgical procedures, it is common that a fibroid, cyst, tumor, or other affected tissue is required to be removed. In these and other procedures where potentially cancerous tissue is required to be removed, removal of the tissue specimen(s) in an enclosed environment is highly desirable to inhibit seeding of cancer cells. Thus, with respect to breaking down large tissue specimens for removal through minimally-invasive openings, there is the added challenge of doing so within an enclosed environment.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is a device facilitating removal of a tissue specimen from an internal body cavity. The device includes a sheath defining a proximal end portion and a distal end portion, and a deployable assembly selectively deployable from the distal end portion of the sheath. The deployable assembly, more specifically, is deployable from a retracted position, wherein the deployable assembly is disposed within the distal end portion of the sheath, to a deployed condition, wherein the deployable assembly extends distally from the distal end portion of the sheath. The deployable assembly includes a funnel defining an interior, a proximal apex portion, and a distal base portion having an annular perimeter. The deployable assembly further includes a plurality of guards, each defining a fixed end attached to a portion of the annular perimeter of the distal base portion of the funnel by a living hinge. In the deployed condition of the deployable assembly, the guards are disposed in a presented condition wherein the guards extend radially inwardly from the annular perimeter of the distal base portion of the funnel in overlapping relation relative to one another such that the guards extend across the distal base portion of the funnel to enclose the interior of the funnel.

In an aspect of the present disclosure, the living hinges bias the guards towards the presented condition. In such aspects, in response to sufficient proximal urging, the guards are configured to deflect inwardly in the interior of the funnel against the bias of the living hinges from the presented condition to a contracted condition. The living hinges may define one-way configurations such that outward deflection of the guards from the presented condition is inhibited.

In another aspect of the present disclosure, the funnel includes a plurality of spaced-apart layers defining at least one interior chamber. In such aspects, the funnel, more specifically, may include an inner layer, an intermediate layer, and an outer layer. The funnel may further define a first interior chamber between the inner and intermediate layers and a second interior chamber between the intermediate and outer layers.

In still another aspect of the present disclosure, an outflow line communicates with the first interior chamber and is configured to supply fluid thereto to deploy the deployable assembly from the retracted condition to the deployed condition.

In yet another aspect of the present disclosure, an inflow line communicates with the second interior chamber and is configured to withdraw fluid therefrom to return the deployable assembly towards the retracted condition. In such aspects, the first and second interior chambers are disposed in fluid communication with one another.

In still yet another aspect of the present disclosure, the sheath defines a lumen extending therethrough. The lumen of the sheath communicates with the interior of the funnel in the deployed condition of the deployable assembly such that, for example, a surgical tool may be inserted through the lumen and into the interior of the funnel.

A system for removal of a tissue specimen from an internal body cavity provided in accordance with aspects of the present disclosure includes an endoscope, an outer assembly, and a surgical tool. The endoscope includes an elongated sheath defining a lumen therethrough. The outer assembly is configured to releasably engage the endoscope and includes an outer sheath and a deployable assembly. The outer sheath defines a proximal end portion and a distal end portion and is configured for positioning about the elongated sheath of the endoscope to define an annular channel therebetween. The deployable assembly is selectively deployable from the distal end portion of the outer sheath and includes a funnel and a plurality of guards. The funnel defines an interior, a proximal apex portion, and a distal base portion having an annular perimeter. Each guard defines a fixed end attached to a portion of the annular perimeter of the distal base portion of the funnel. In the deployed condition of the deployable assembly, the guards are disposed in a presented condition wherein the guards extend radially inwardly from the annular perimeter of the distal base portion of the funnel in overlapping relation relative to one another such that the guards extend across the distal base portion of the funnel to enclose the interior of the funnel. The surgical tool is insertable through the lumen of the elongated sheath of the endoscope such that a portion of the surgical tool extends distally from the elongated sheath and into the interior of the funnel.

In an aspect of the present disclosure, the guards are biased towards the presented condition and, in response to sufficient proximal urging, are deflectable inwardly in the interior of the funnel against the bias from the presented condition to a contracted condition to permit passage of a tissue specimen into the interior of the funnel.

In another aspect of the present disclosure, the guards define one-way configurations such that the guards are inhibited from deflecting outwardly relative to the funnel from the presented condition, thereby inhibiting expulsion of a tissue specimen from the interior of the funnel.

In still another aspect of the present disclosure, the surgical tool is a rotary reciprocating morcellator.

In yet another aspect of the present disclosure, the endoscope further includes a visualization device configured to enable visualization of the interior of the funnel.

In still yet another aspect of the present disclosure, the endoscope is configured to deliver fluid into the interior of the funnel or remove fluid from the interior of the funnel. Alternatively or additionally, the annular channel defined between the outer sheath of the outer assembly and the elongated sheath of the endoscope may enables fluid to be delivered into the interior of the funnel or removed from the interior of the funnel.

In another aspect of the present disclosure, the system further includes a containment bag configured for positioning about the deployable assembly and a portion of the outer sheath.

A method for removal of a tissue specimen from an internal body cavity provided in accordance with aspects of the present disclosure includes deploying a deployable assembly from a retracted position, wherein the deployable assembly is disposed within a distal end portion of a sheath, to a deployed condition, wherein the deployable assembly extends distally from the distal end portion of the sheath. The deployable assembly includes a funnel and a plurality of guards extending across a base portion of the funnel to enclose an interior of the funnel. The method further includes passing a tissue specimen into the interior of the funnel by deflecting the guards inwardly into the interior of the funnel, returning the guards such that the guards extend across the base portion of the funnel to enclose the tissue specimen within the interior of the funnel, inserting a surgical tool through the sheath and into the interior of the funnel, and morcellating the tissue specimen using the surgical tool. The morcellated tissue specimen is removed through the surgical tool.

In an aspect of the present disclosure, after returning the guards, a containment bag is disposed about the deployable assembly.

In another aspect of the present disclosure, during morcellation, fluid is pumped into and withdrawn from the interior of the funnel.

In yet another aspect of the present disclosure, prior to inserting the surgical tool, an endoscope is inserted through the sheath. In such aspects, the surgical tool is inserted through the endoscope and into the interior of the funnel, and the endoscope includes a visualization device enabling visualization of the interior of the funnel to facilitate morcellating the tissue specimen.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements and.

DETAILED DESCRIPTION

The present disclosure provides devices, systems, and methods facilitating break down and removal of a tissue specimen from an internal body cavity.

Figure 1:
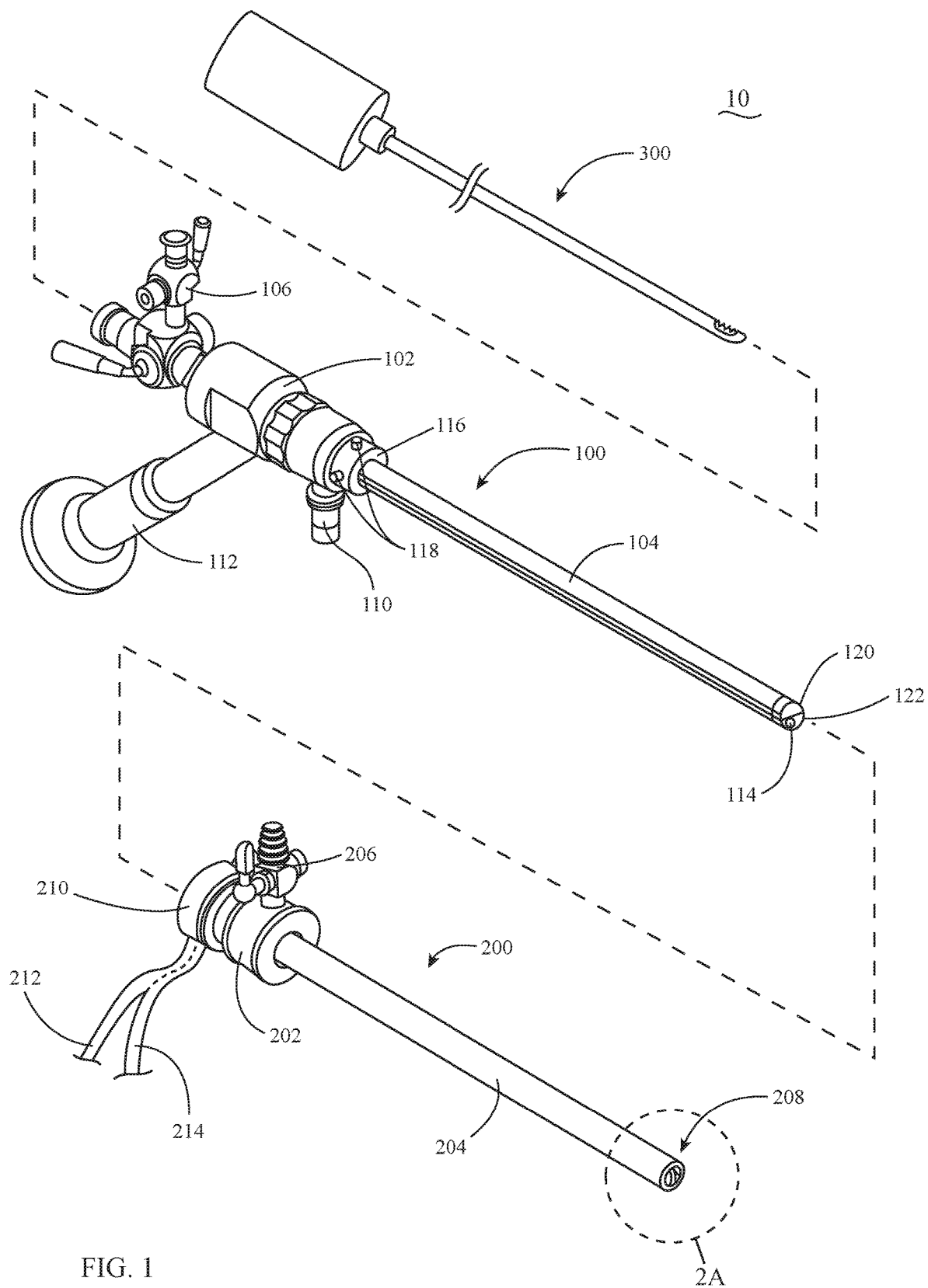
FIG. 1 is an exploded, perspective view of a tissue specimen removal system provided in accordance with the present disclosure.

Turning to FIG. 1, a system 10 generally includes an endoscope 100 (which, in embodiments, may be configured as a hysteroscope for use in tissue specimen removal from the uterine cavity), an outer assembly 200 removably engagable about endoscope 100, and a surgical tool 300 removably insertable through endoscope 100.

Endoscope 100 includes a proximal body 102, an elongated sheath 104 extending distally from proximal body 102, an outflow valve 106 mounted on proximal body 102, a light post 110 extending transversely from proximal body 102, a visualization arm 112 obliquely angled relative to proximal body 102 and extending therefrom, and a visualization device 114 extending through elongated sheath 104.

Proximal body 102 of endoscope 100 includes a distal collar 116 including suitable engagement features, e.g., engagement pegs 118, configured to enable releasable engagement of outer assembly 200 with proximal body 102 of endoscope 100.

Elongated sheath 104 of endoscope 100 extends through distal collar 116 of proximal body 102 and distally from proximal body 102. Elongated sheath 104 defines an interior lumen bifurcated into a first lumen portion 120 and a second lumen portion 122, although other suitable configurations are also contemplated.

Outflow valve 106 is disposed in fluid communication with first lumen portion 120 of elongated sheath 104, second lumen portion 122 of elongated sheath 104, or both first and second lumen portions 120, 122 of elongated sheath 104, to enable the selective supply of fluid, e.g., saline, through elongated sheath 104 and out the open distal end thereof. To this end, outflow valve 106 may operably couple to a fluid pump (not shown). Outflow valve 106 may alternatively be configured as the inflow valve.

Visualization device 114 extends through one of the lumen portions 120, 122 of elongated sheath 104, e.g., second lumen portion 122, to the distal end thereof. Visualization device 114 can include fiber-optic technology for illumination and image transmission and is disposed in communication with visualization arm 112. Visualization arm 112, in turn, is configured to connect to an imaging device, e.g., a camera (not shown), to capture images received via visualization device 114.

Continuing with reference to FIG. 1, outer assembly 200 includes a proximal hub 202, an outer sheath 204 extending distally from proximal hub 202, an inflow valve 206 mounted on proximal hub 202, and a deployable assembly 208 operably coupled to outer sheath 204 and configured for selective deployment distally therefrom.

Proximal hub 202 includes a proximal collar 210 including suitable engagement features, e.g., engagement slots (not shown), configured to releasably engage engagement pegs 118 of distal collar 116 of proximal body 102 of endoscope 100, thus enabling releasable engagement of outer assembly 200 with proximal body 102 of endoscope 100. When outer assembly 200 is engaged about endoscope 100, outer sheath 204 is disposed about elongated sheath 104 of endoscope 100 so as to define an annular gap therebetween. Further, when outer assembly 200 is engaged about endoscope 100, inflow valve 206 operable communicates with the annular gap defined between elongated sheath 104 of endoscope 100 and outer sheath 204 of outer assembly 200 to enable the selective withdrawal of fluid, e.g., saline, bodily fluids, and debris, from adjacent the distal end portion of outer assembly 200. To this end, inflow valve 206 may operably couple to a suction source (not shown). Inflow valve 206 may alternatively be configured as the outflow valve.

Deployable assembly 208 is initially disposed within the distal end portion of outer sheath 204 of outer assembly 200, in a retracted condition thereof (FIGS. 1 and 2A), and is selectively deployable therefrom to a deployed condition (FIG. 2B) thereof. Outflow and inflow lines 212, 214, respectively, are operably coupled to proximal hub 202 of outer assembly 200 and communicate with deployable assembly 208 to enable the selective deployment and retraction thereof. For example, outer sheath 204 may be formed from a plurality of sheath layers 204a-204c (FIG. 3) so as to define an outflow annular channel 216 (FIG. 3) and an inflow annular channel 218 (FIG. 3) within outer sheath 204, although other configurations are also contemplated. Outflow and inflow lines 212, 214 are further coupled to a fluid pump (not shown) as part of a closed-loop system to enable the supply of fluid to and withdrawal of fluid from outflow and inflow lines 212, 214, respectively, although other configurations are also contemplated, e.g., open loop systems. Deployable assembly 208 is described in greater detail below.

Referring still to FIG. 1, surgical tool 300 may be any suitable tool configured to facilitate breakdown and/or removal of tissue. For example, surgical tool 300 can be a rotary morcellator, a reciprocating morcellator, or a morcellator having both reciprocal and rotary capabilities (as shown). Other suitable morcellators (configured to mechanically and/or electrically cut tissue) or other suitable surgical cutting instruments are also contemplated. Surgical tool 300, in use, is configured for insertion through first lumen portion 120 of elongated sheath 104 of endoscope 100 and, when fully inserted, may extend distally therefrom (see FIG. 4D).

Figure 2A:
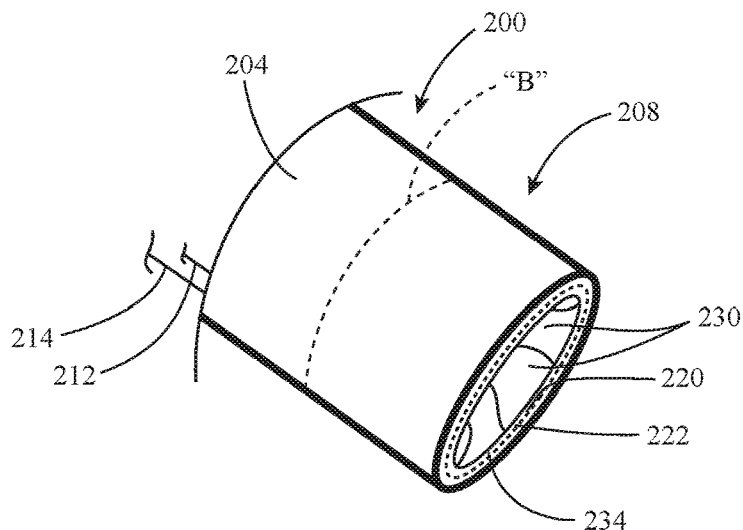
FIG. 2A is an enlarged, perspective view of the area of detail indicated as "2A" in FIG. 1, wherein a distal end portion of the outer assembly of the system of FIG. 1 is disposed in a retracted condition.
Figure 2B:
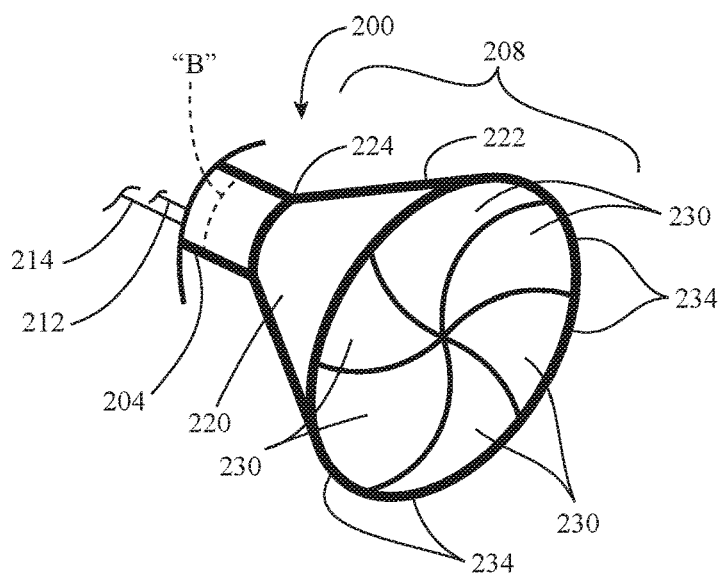
FIG. 2B is a perspective view of the distal end portion of the outer assembly of the system of FIG. 1, disposed in a deployed condition.
Figure 3:
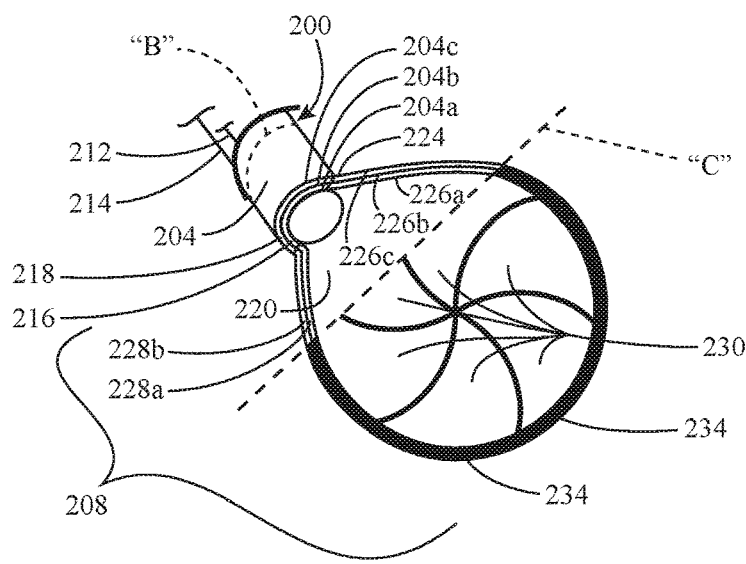
FIG. 3 is a perspective, cut-away view of the distal end portion of the outer assembly of the system of FIG. 1, disposed in the deployed condition and having portions removed (as indicated by cutline "C-C") to illustrate the internal features thereof.

Turning to FIGS. 2A, 2B, and 3, as noted above, deployable assembly 208 is transitionable from a retracted condition (FIG. 2A), wherein deployable assembly 208 is disposed within the distal end portion of outer sheath 204 of outer assembly 200, to a deployed condition (FIG. 2B), wherein deployable assembly 208 extends distally from the distal end portion of outer sheath 204 of outer assembly 200. Deployable assembly 208 includes a funnel 220 and a plurality of guards 230, and may be integral with outer assembly 200, affixed thereto, or releasably engagable therewith. In embodiments where deployable assembly 208 is releasably engagable with outer assembly 200, deployable assembly 208 and a portion of outer sheath 204 may be configured to break-away from the remainder of outer sheath 204 along break line "B," e.g., in response to actuation of a disengagement mechanism (not shown).

Funnel 220 of deployable assembly 208, once deployed from the distal end portion of outer sheath 204, is oriented such that a base portion 222 of funnel 220 is more distally-disposed, while an apex portion 224 of funnel 220 is more-proximally disposed. Funnel 220 is formed such that, in the retracted condition (FIG. 2A) of deployable assembly 208, funnel 220 is capable of being folded, rolled, and/or otherwise contracted to enable positioning within the distal end portion of outer sheath 204, and such that, in the deployed condition (FIG. 2B) of deployable assembly 208, funnel 220 assumes its funnel-shaped configuration and extends distally from outer sheath 204. This may be achieved, for example, by forming funnel 220 from a semi-rigid and semi-flexible material, forming funnel 220 from both flexible and rigid portions, and/or including structural supports, e.g., bands, ribs, etc., on or within a flexible body of funnel 220. Further, it is contemplated that funnel 220 be configured to resist puncture and tearing such as, for example, in response to accidental contact of surgical tool 300 (FIG. 1) therewith.

With particular reference to FIG. 3, funnel 220 is formed from multiple spaced-apart layers including an inner layer 226a, an intermediate layer 226b, and an outer layer 226c. As a result of this configuration of spaced-apart layers, a first chamber 228a is defined between the inner and intermediate layers 226a, 226b, respectively, and a second chamber 228b is defined between the intermediate and outer layers 226b, 226c, respectively. The inner and outer layers 226a, 226c are joined with one another at the base portion 222 of funnel 220 about the perimeter thereof to seal off first and second chambers 228a, 228b from the exterior thereof. Intermediate layer 226b, however, does not extend fully to the distal end of base portion 222 of funnel 220. As such, the perimeter of base portion 222 of funnel 220 enables fluid communication between first and second chambers 228a, 228b.

Layers 226a, 226b, 226c of funnel 220 may be integral with or otherwise coupled to, sheath layers 204a, 204b, 204c, respectively, of outer sheath 204, such that outflow annular channel 216 and inflow annular channel 218 communicate with first and second chambers 228a, 228b, respectively. Thus, fluid can be delivered to first chamber 228a via outflow line 212 and outflow annular channel 216, and fluid may be returned from second chamber 228b via inflow annular channel 218 and inflow line 214. As noted above, outflow and inflow lines 212, 214 are further coupled to a fluid pump (not shown), thus enabling the supply of fluid to and withdrawal of fluid from first and second chambers 228a, 228b, respectively. Alternatively, the above-detailed configuration of inflow and outflow may be reversed.

The initial pumping of fluid through outflow line 212, outflow annular channel 216, and into first and second chambers 228a, 228b may serve to urge deployable assembly 208 from the retracted condition (FIG. 2A) to the deployed condition (FIG. 2B), thereby deploying funnel 220. Once funnel 220 has been deployed, first and second chambers 228a, 228b may be maintained in a fluid-filled condition (by maintaining sufficient inflow and outflow or preventing both inflow and outflow), serving to maintain pressure to maintain the shape of funnel 220 in the deployed condition (FIG. 2B) of deployable assembly 208 and providing structural stability thereto. After use, the supply of fluid via outflow line 212 and outflow annular channel 216 to funnel 220 is terminated such that deployable assembly 208 and, thus, funnel 220 thereof, are contracted back towards the retracted condition (FIG. 2A). Funnel 220 may be configured to fully return to its initial position in the retracted condition (FIG. 2A) of deployable assembly 208 or may be configured to contract sufficiently so as to enable atraumatic removal from an internal body cavity (without returning fully to its initial position in the retracted condition (FIG. 2A)).

Referring again to FIGS. 2A and 2B, guards 230 of deployable assembly 208 define cantilever configurations attached at the fixed ends thereof about the annular perimeter of base portion 222 of funnel 220 and extending radially inwardly therefrom to the free ends thereof. Guards 230 are arranged in overlapping relation such that, in the deployed condition of deployable assembly 208, guards 230 are able to extend across base portion 222 of funnel 220 to enclose the interior of funnel 220.

The fixed end of each guard 230 may be attached to the annular perimeter of base portion 222 of funnel 220 by way of a living hinge 234, or other suitable coupling, to allow guards 230 to move between a collapsed condition (FIG. 2A), wherein guards 230 are pressed inwardly against the interior surface of funnel 220, and a presented condition (FIG. 2B), wherein guards 230 extend across base portion 222 of funnel 220 to enclose the interior of funnel 220. The living hinges 234 of guards 230 are configured to bias guards 230 towards the presented condition (FIG. 2B). Thus, while guards 230 are initially disposed in the collapsed condition, thus enabling funnel 220 to be retracted within outer sheath 204, corresponding to the retracted condition (FIG. 2A) of deployable assembly 208, guards 230 are biased towards and assume the presented condition upon deployment of funnel 220 in the deployed condition (FIG. 2B) of deployable assembly 208. Further, while guards 230 are deflectable inwardly into funnel 220 from the presented condition against the bias of living hinges 224, e.g., in response to urging against the exterior surfaces of guards 230, guards 230 define a one-way configuration whereby guards 230 are inhibited from deflecting outwardly away from funnel 220 from the presented condition.

Turning to FIGS. 4A-4D, in conjunction with FIGS. 1-3, the use of system 10 in the removal of a tissue specimen "S" from an internal body cavity "C" is described. System 10 may be similarly used in the removal of other tissue specimen from other internal body cavities.

Figure 4B:
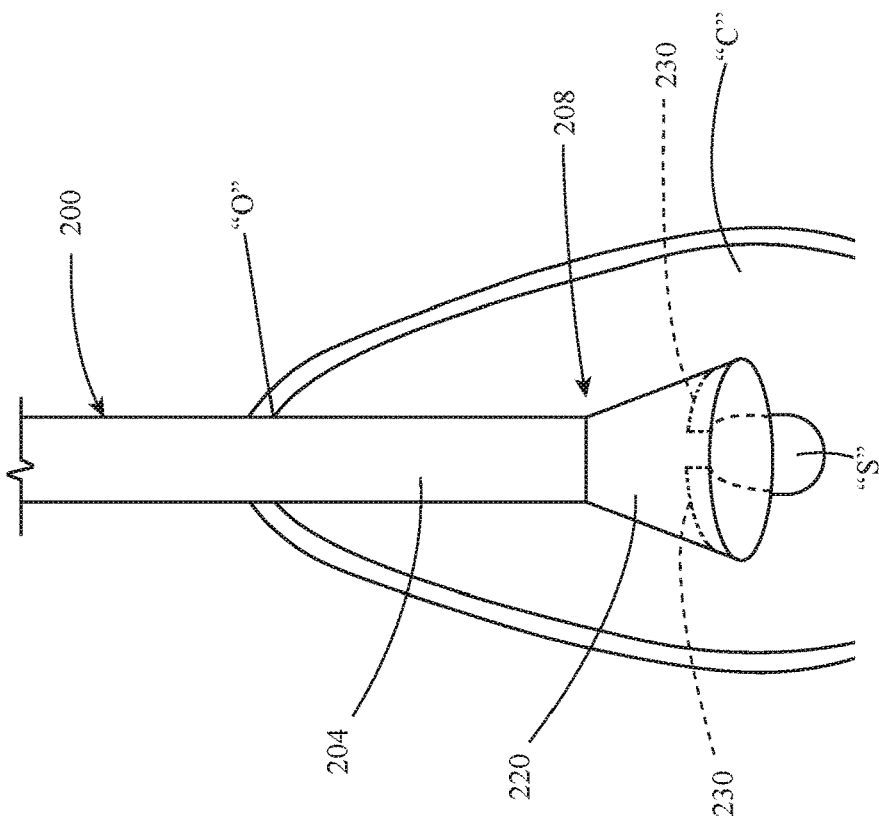
FIGS. 4A-4D illustrate use of the system of FIG. 1 for removing a tissue specimen from an internal body cavity.
Figure 4A:
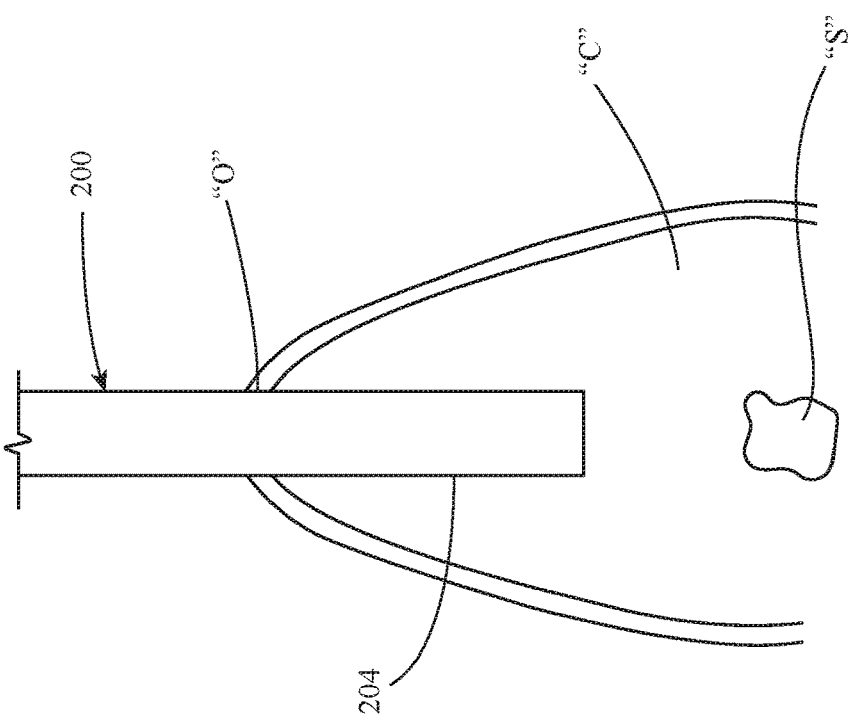

Referring initially to FIG. 4A, with deployable assembly 208 of outer assembly 200 disposed in the retracted condition (FIG. 2A), outer assembly 200 is advanced through a surgically created or naturally occurring opening "O" into the cavity "C." Outer assembly 200 may be inserted into the cavity "C" together with endoscope 100 (FIG. 1) or prior to engagement of endoscope 100 (FIG. 1) therewith. Further, outer assembly 200 may be inserted directly or may be inserted through a port (not shown). Additionally or alternatively, insertion of outer assembly 200 may be facilitated through the use of a trocar (not shown) disposed within outer assembly 200.

With reference to FIG. 4B, once outer assembly 200 is disposed within the cavity "C," deployable assembly 208 may be deployed from outer assembly 200 such that funnel 220 is transitioned to the deployed condition and such that guards 230 are moved to the presented condition. As noted above, the supply of fluid to funnel 220 via outflow line 212 and outflow annular channel 216 may deploy funnel 220 to the deployed condition, which allows guards 230 to move the presented condition as or soon after funnel 220 is deployed.

Continuing with reference to FIG. 4B, with funnel 220 disposed in the deployed condition and guards 230 disposed in the presented condition, outer assembly 200 may be advanced towards a specimen "S" to be removed and/or the specimen "S" may be moved towards outer assembly 200, e.g., using a grasper (not shown) inserted through an abdominal port. Outer assembly 200 and/or specimen "S," more specifically, are moved towards one another until the specimen "S" contacts guards 230 and applies suitable force thereto to urge guards 230 inwardly into funnel 220 towards the collapsed condition, thus allowing specimen "S" to enter funnel 220.

Figure 4D:
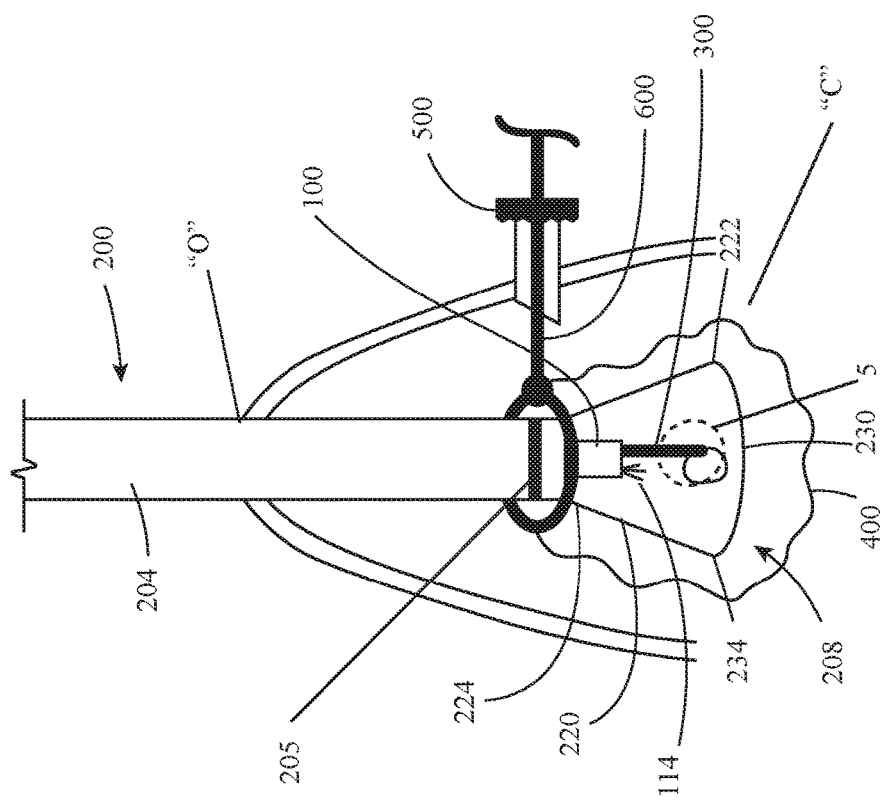
Figure 4C:
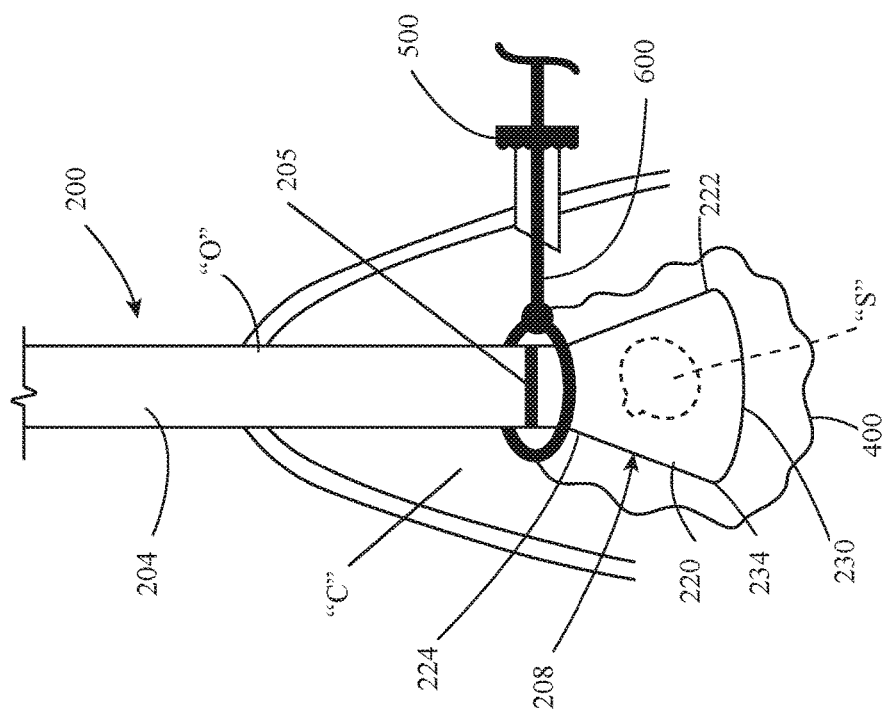

Referring to FIG. 4C, once specimen "S" is fully positioned within funnel 220 and clears guards 230, guards 230 are permitted to return, under bias, back to the presented condition, wherein guards 230 extend across base portion 222 of funnel 220 to enclose specimen "S" within the interior of funnel 220. With funnel 220 fully enclosing the specimen "S" within the interior thereof, a containment bag 400 may be deployed about funnel 220 and the distal end portion of outer assembly 200. Containment bag 400 may be inserted into the cavity "C" via a port 500, and may be deployed about funnel 220 and the distal end portion of outer sheath 204 of outer assembly 200 using a suitable deployment apparatus 600. Alternatively, containment bag 400 and deployment apparatus 600 may be operably disposed about outer sheath 204 of outer assembly 200 towards the distal end portion thereof, or may be coupled to an outer deployment tube (not shown) disposed about outer sheath 204, to enable containment bag 400 to be deployed distally from outer sheath 204 about funnel 220. Once containment bag 400 surrounds funnel 220 and the distal end portion of outer sheath 204, the open end of containment bag 400 may be cinched about the distal end portion of outer sheath 204 to form a substantially fluid-tight seal, thereby sealing funnel 220 within containment bag 400. To this end, an annular divot 205 may be defined within the exterior surface of outer sheath 204 towards the distal end portion thereof to facilitate cinching the open end of containment bag 400 about outer sheath 204 and to "lock" the open end of containment bag 400 in position about outer sheath 204.

Turning to FIG. 4D, with containment bag 400 sealed about funnel 220 and the distal end portion of outer sheath 204, if not done so already, endoscope 100 is inserted into outer assembly 200 and engaged therewith such that elongated sheath 104 extends through outer sheath 204. Thereafter, surgical tool 300 is inserted through endoscope 100 (and, thus, through outer assembly 200) and into funnel 220 adjacent the specimen "S." Before or after insertion of surgical tool 300, funnel 220 may be filled with fluid, e.g., saline, pumped into funnel 220 from first and/or second lumen portions 120, 122 of elongated sheath 104, via outflow valve 106. More specifically, continuous flow may be achieved by simultaneously pumping fluid into funnel 220 via outflow valve 106 and withdrawing fluid from funnel 220 through the annular gap defined between elongated sheath 104 of endoscope 100 and outer sheath 204 of outer assembly 200 and, ultimately out through inflow valve 206. Additionally or alternatively, fluid may be withdrawn through surgical tool 300 during use thereof, as detailed below.

Figure 5:
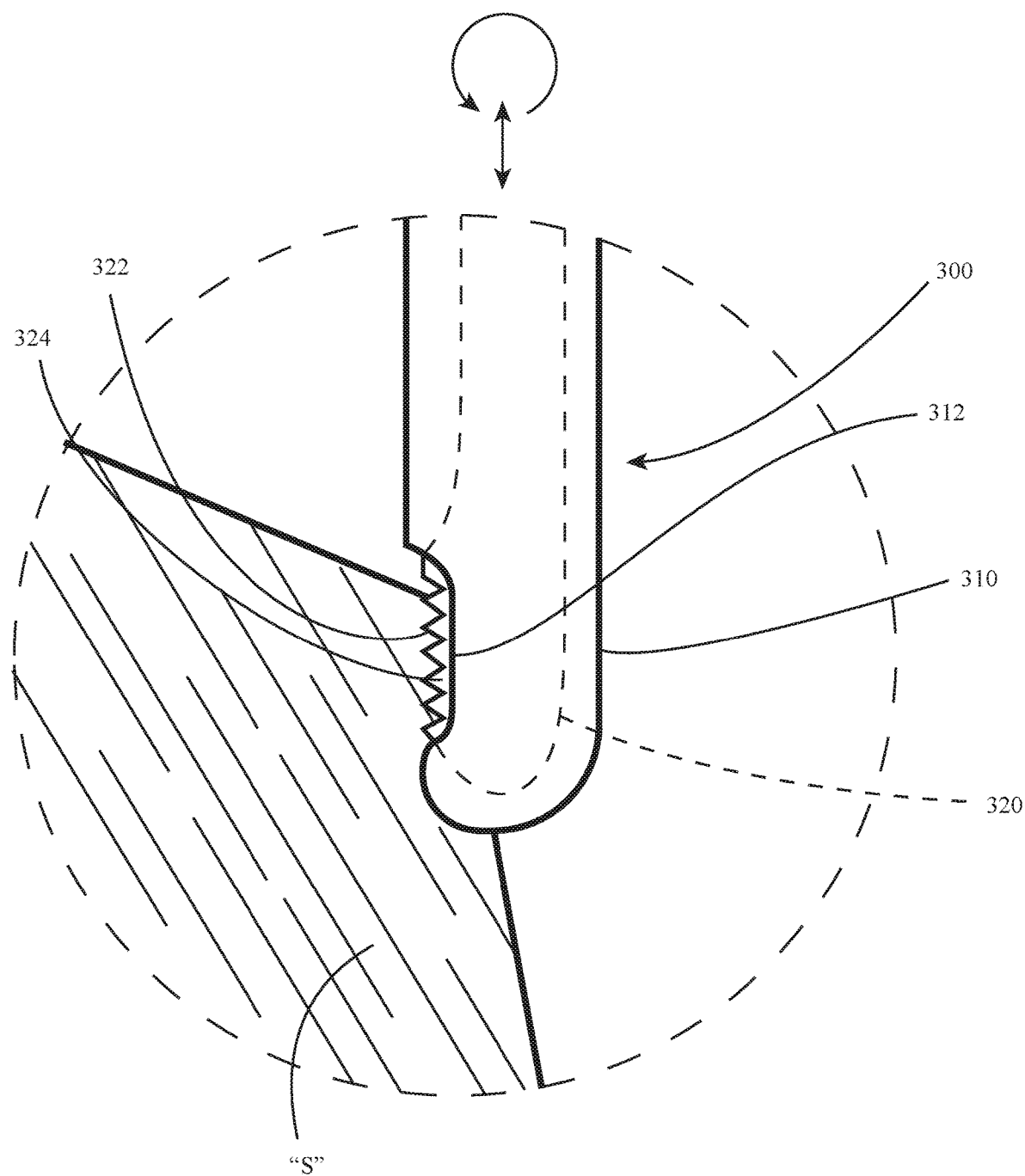
FIG. 5 is an enlarged view of the area of detail indicated as "5" in FIG. 4D.

With additional reference to FIG. 5, with surgical tool 300 positioned within funnel 220 adjacent the specimen "S" and fluid disposed within and/or continuously flowing through funnel 220, tool 300 may be activated. As noted above, surgical tool 300 can be a morcellator having both reciprocal and rotary capabilities. In such embodiments, surgical tool 300 may, more specifically, include a fixed outer tube 310 and a movable inner tube 320 disposed within fixed outer tube 310 and configured to both rotate and reciprocate relative to inner tube 320. Fixed outer tube 310 defines a window 312 providing access to movable inner tube 320. Movable inner tube 320 defines a cutting edge 322, e.g., a serrated cutting edge, surrounding a window 324 thereof. Further, surgical tool 300 is configured to connect to a suction source (not shown) such that, in use, tissue may be suctioned through window 312 of fixed outer tube 310 and window 324 of movable inner tube 320, thus enabling cutting of that tissue with cutting edge 322 via the rotating and reciprocating motion of movable inner tube 320 relative to fixed outer tube 310. Morcellation of tissue using surgical tool 300 may be performed under guidance from visualization device 114 of endoscope 100. Once morcellated, the smaller tissue fragments of specimen "S" are suctioned through movable inner tube 320 of surgical tool 300 to a collection reservoir (not shown).

Once the tissue specimen "S" is sufficiently morcellated and removed (wholly or partially), surgical tool 300 and endoscope 100 may be removed from the cavity "C." Thereafter, outer assembly 200 is returned (fully or partially) towards the retracted condition and containment bag 400 is released from its deployment apparatus 600 to enable withdrawal of outer assembly 200 together with containment bag 400 from the cavity "C." Alternatively, in embodiments where deployable assembly 208 is removable from outer sheath 204 of outer assembly 200, deployable assembly 208 may be released therefrom after retraction of funnel 220 such that outer assembly 200 may be removed through the opening "O" while containment bag 400, with deployable assembly 208 sealingly enclosed therein, may be removed through port 500 using deployment apparatus 600.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A device facilitating removal of a tissue specimen from an internal body cavity, the device comprising:
    a sheath having a proximal end portion and a distal end portion; and
    a deployable assembly selectively deployable from the distal end portion of the sheath from a retracted condition, wherein the deployable assembly is disposed within the distal end portion of the sheath, to a deployed condition, wherein the deployable assembly extends distally from the distal end portion of the sheath, the deployable assembly including:
        a funnel having an interior, a proximal apex portion, and a distal base portion having an annular perimeter; and
        a plurality of guards, each guard having a fixed end attached to a portion of the annular perimeter of the distal base portion of the funnel by a living hinge, wherein, in the deployed condition of the deployable assembly, the guards are disposed in a presented condition wherein the guards extend radially inwardly from the annular perimeter of the distal base portion of the funnel in overlapping relation relative to one another such that the guards extend across the distal base portion of the funnel to enclose the interior of the funnel.

2. The device according to claim 1, wherein the living hinges bias the guards towards the presented condition, and wherein the guards, in response to sufficient proximal urging, are configured to deflect inwardly in the interior of the funnel against the bias of the living hinges from the presented condition to a contracted condition.

3. The device according to claim 2, wherein the living hinges have one-way configurations such that outward deflection of the guards from the presented condition is inhibited.

4. The device according to claim 1, wherein the funnel includes a plurality of spaced-apart layers having at least one interior chamber.

5. The device according to claim 4, wherein the funnel includes an inner layer, an intermediate layer, and an outer layer, and wherein the funnel has a first interior chamber between the inner and intermediate layers and a second interior chamber between the intermediate and outer layers.

6. The device according to claim 5, further comprising an outflow line communicating with the first interior chamber and configured to supply fluid thereto to deploy the deployable assembly from the retracted condition to the deployed condition.

7. The device according to claim 6, further comprising an inflow line communication with the second interior chamber and configured to withdraw fluid therefrom to return the deployable assembly towards the retracted condition, wherein the first and second interior chambers are disposed in fluid communication with one another.

8. The device according to claim 7, wherein the sheath has a lumen extending therethrough, the lumen communication with the interior of the funnel in the deployed condition of the deployable assembly.

9. A system for removal of a tissue specimen from an internal body cavity, the system comprising:
    an endoscope including an elongated sheath having a lumen therethrough;
    an outer assembly releasably engaged with the endoscope, the outer assembly including:
        an outer sheath having a proximal end portion and a distal end portion and configured for positioning about the elongated sheath of the endoscope to define an annular channel therebetween; and
        a deployable assembly selectively deployable from the distal end portion of the outer sheath from a retracted condition, wherein the deployable assembly is disposed within the distal end portion of the sheath, to a deployed condition, wherein the deployable assembly extends distally from the distal end portion of the sheath, the deployable assembly including:
            a funnel having an interior, a proximal apex portion, and a distal base portion having an annular perimeter; and
            a plurality of guards, each guard having a fixed end attached to a portion of the annular perimeter of the distal base portion of the funnel by a living hinge, wherein, in the deployed condition of the deployable assembly, the guards are disposed in a presented condition wherein the guards extend radially inwardly from the annular perimeter of the distal base portion of the funnel in overlapping relation relative to one another such that the guards extend across the distal base portion of the funnel to enclose the interior of the funnel; and a surgical tool insertable through the lumen of the elongated sheath of the endoscope such that a portion of the surgical tool extends distally from the elongated sheath and into the interior of the funnel.

10. The system according to claim 9, wherein the guards are biased towards the presented condition, and wherein the guards, in response to sufficient proximal urging, are deflectable inwardly in the interior of the funnel against the bias from the presented condition to a contracted condition to permit passage of a tissue specimen into the interior of the funnel.

11. The system according to claim 10, wherein the guards have one-way configurations such that the guards are inhibited from deflecting outwardly relative to the funnel from the presented condition, thereby inhibiting expulsion of a tissue specimen from the interior of the funnel.

12. The system according to claim 9, wherein the surgical tool is a rotary reciprocating morcellator.

13. The system according to claim 9, wherein the endoscope further includes a visualization device configured to enable visualization of the interior of the funnel.

14. The system according to claim 9, wherein the endoscope is configured to deliver fluid into the interior of the funnel or remove fluid from the interior of the funnel.

15. The system according to claim 14, wherein the annular channel defined between the outer sheath of the outer assembly and the elongated sheath of the endoscope enables fluid to be delivered into the interior of the funnel or removed from the interior of the funnel.

16. The system according to claim 9, further comprising a containment bag configured for positioning about the deployable assembly and a portion of the outer sheath.

* * * * *